United States Patent [19]

Rütter et al.

[11] Patent Number: 5,773,657
[45] Date of Patent: Jun. 30, 1998

[54] HYDROGENATION OF AROMATIC COMPOUNDS IN WHICH AT LEAST ONE AMINO GROUP IS BONDED TO AN AROMATIC NUCLEUS

[75] Inventors: Heinz Rütter, Hochdorf-Assenheim; Thomas Rühl, Frankenthal; Boris Breitscheidel, Fulda; Jochem Henkelmann, Mannheim; Andreas Henne, Neustadt; Thomas Wettling, Limburgerhof, all of Germany

[73] Assignee: BASF Aktiengesellschaft, Ludwigshafen, Germany

[21] Appl. No.: 702,262

[22] Filed: Aug. 23, 1996

[51] Int. Cl.$^6$ ................................... C07V 209/72
[52] U.S. Cl. .................. 564/450; 564/451; 502/313; 502/330
[58] Field of Search ................ 546/450, 451; 502/313, 330

[56] References Cited

U.S. PATENT DOCUMENTS

| | | | |
|---|---|---|---|
| 2,606,925 | 8/1952 | Whitman | 260/563 |
| 2,822,392 | 2/1958 | Illich et al. | 260/563 |
| 3,636,108 | 1/1972 | Brake | 260/563 |
| 3,697,449 | 10/1972 | Brake | 252/474 |
| 4,394,523 | 7/1983 | Allen et al. | 564/451 |
| 4,952,549 | 8/1990 | Immel et al. | 502/330 |
| 5,023,226 | 6/1991 | Immell et al. | 502/313 |
| 5,360,934 | 11/1994 | Vedage et al. | 544/451 |

FOREIGN PATENT DOCUMENTS

| | | |
|---|---|---|
| 67058 | 10/1984 | European Pat. Off. . |
| 501265 | 9/1992 | European Pat. Off. . |

Primary Examiner—Brian M. Burn
Attorney, Agent, or Firm—John H. Shurtleff

[57] ABSTRACT

Aromatic compounds in which at least one amino group is bonded to an aromatic nucleus are catalytically hydrogenated in the liquid phase by a process in which the catalyst consists essentially of ruthenium and, optionally at least one metal of subgroup I, VII or VIII in an amount of from 0.01 to 30% by weight, based on the total weight of the catalyst, applied to a carrier which has a mean pore diameter of at least 0.1 μm and a surface area of not more than 15 m$^2$/g.

24 Claims, No Drawings

HYDROGENATION OF AROMATIC COMPOUNDS IN WHICH AT LEAST ONE AMINO GROUP IS BONDED TO AN AROMATIC NUCLEUS

The present invention relates to a process for hydrogenating aromatic compounds in which at least one amino group is bonded to an aromatic nucleus.

The present invention relates in particular to a process for the monohydrogenating aromatic amines and diamines. The mononuclear or polynuclear, unsubstituted or substituted aromatic amines and diamines are hydrogenated to the corresponding cycloaliphatic amines and diamines with the aid of catalysts which contain ruthenium and, if required, at least one further metal of subgroup I, VII or VIII on a carrier.

Cycloaliphatic amines, in particular unsubstituted cyclohexylamines and dicyclohexylamines, are used for the preparation of antiaging agents for rubbers and plastics, as corrosion inhibitors and as intermediates for crop protection agents and textile assistants. Cycloaliphatic diamines are furthermore used in the preparation of polyamide and polyurethane resins and are also used as curing agents for epoxy resins.

It is known that cycloaliphatic amines or diamines can be prepared by catalytic hydrogenation of the corresponding mononuclear or polynuclear aromatic amines or diamines. Hydrogenation of aromatic amines and diamines to the corresponding cycloaliphatic amines and diamines in the presence of hydrogenation catalysts, in particular catalysts applied to carriers, has been described in many publications.

The catalysts used were, for example, Raney cobalt containing basic additives (JP 43/3180), nickel catalysts (U.S. Pat. No. 4,914,239, German Patent 805,518), rhodium catalysts (BE 739376, JP 7019901, JP 7235424) and palladium catalysts (U.S. Pat. No. 3,520,928, EP 501 265, EP 53 181, JP 59/196843). Ruthenium catalysts (U.S. Pat. No. 3,697,449, U.S. Pat. No. 3,636,108, U.S. Pat. No. 2,822,392, U.S. Pat. No. 2,606,925, EP 501 265, EP 324 984, EP 67 058, DE 21 32 547 and German Laid-Open Application DOS 1,106,319) are also used.

DE 21 32 547 discloses a process for hydrogenating mononuclear or polynuclear aromatic diamines to the corresponding cycloaliphatic amines, which is carried out in the presence of suspended ruthenium catalysts.

EP 67 058 describes a process for the preparation of cyclohexylamine by catalytic hydrogenation of the corresponding aromatic amine. The catalyst used is ruthenium metal in a finely divided form on activated aluminum pellets. After being recycled four times, the catalyst began to lose its efficiency.

It is an object of the present invention to provide a process for hydrogenating compounds in which at least one amino group is bonded to an aromatic nucleus, the process being capable of being carried out in particular without removal, working up and recycling of the catalyst.

It is a further object of the present invention to provide a process for hydrogenating aromatic compounds in which at least one amino group is bonded to an aromatic nucleus to give the corresponding cycloaliphatic compounds, only a minimum amount of byproducts being produced.

It is a further object of the present invention to provide a process for hydrogenating aromatic compounds in which at least one amino group is bonded to an aromatic nucleus, high catalyst space velocities and long catalyst lives being permitted.

We have found that the above objects are achieved by a process for hydrogenation as claimed in the claims.

With the novel process, the aromatic compounds in which at least one amino group is bonded to an aromatic nucleus can be hydrogenated with high selectivity to give the corresponding cycloaliphatic compounds.

In particular, the formation of deamination products, for example cyclohexanes or partially hydrogenated dimerization products, such as phenylcyclohexylamines, is preferably virtually completely avoided.

In addition, high catalyst space velocities and long catalyst lives can preferably be achieved. The catalyst space velocity is the space/time yield of the process, ie. the amount of starting material converted per unit time and per amount of catalyst present. The life means the time or the amount of converted starting material which a catalyst withstands without losing its properties and without the product properties significantly changing.

COMPOUNDS

With the novel process, aromatic compounds in which at least one amino group is bonded to an aromatic nucleus can be hydrogenated to give the corresponding cycloaliphatic compounds. The aromatic compounds may be mononuclear or polynuclear aromatic compounds. The aromatic compounds contain at least one amino group which is bonded to an aromatic nucleus. Preferably, the aromatic compounds are aromatic amines or diamines. The aromatic compounds may be substituted on the aromatic nucleus or the aromatic nuclei or on the amino group by one or more alkyl and/or alkoxy radicals, preferably $C_{1-20}$-alkyl and/or alkoxy, particularly preferably $C_{1-10}$-alkyl, in particular methyl, ethyl, propyl, isopropyl, butyl, isobutyl or tert-butyl; among the alkoxy radicals, $C_{1-8}$-alkoxy radicals are preferred. The aromatic nucleus or the aromatic nuclei and the alkyl and alkoxy radicals may be unsubstituted or substituted by halogen, in particular fluorine, or may have other suitable inert substituents.

The aromatic compounds in which at least one amino group is bonded to an aromatic nucleus may also have a plurality of aromatic nuclei which are linked via an alkyl radical, preferably a methylene group. The linking alkyl chain, preferably methylene group, may have one or more alkyl substituents which may be $C_{1-20}$-alkyl, preferably $C_{1-10}$-alkyl, particularly preferably methyl, ethyl, propyl, isopropyl, butyl, sec-butyl or tert-butyl.

The amino group bonded to the aromatic nucleus may likewise be substituted by one or more of the alkyl radicals described above.

Particularly preferred compounds are aniline, naphthylamine, diaminobenzenes, diaminotoluenes and bis-p-aminophenylmethane.

CATALYSTS

The catalysts used according to the invention can be prepared industrially by applying ruthenium and, if required, at least one metal of subgroup I, VII or VIII to a suitable carrier. The application can be achieved by impregnating the catalyst in aqueous metal salt solutions, such as ruthenium salt solutions, by spraying corresponding metal salt solutions onto the carrier or by other suitable methods. Suitable ruthenium salts for the preparation of the ruthenium salt solutions and suitable metal salts of subgroup I, VII or VIII are the nitrates, nitrosylnitrates, halides, carbonates, carboxylates, acetylacetonates, chlorine complexes, nitrito complexes or amine complexes of the corresponding metals, the nitrates and nitrosylnitrates being preferred.

In the case of catalysts which, in addition to ruthenium, contain further metals applied to the carrier, metal salts or metal salt solutions may be applied simultaneously or in succession.

Carriers coated or impregnated with the ruthenium salt solution or metal salt solution are then dried, preferably at from 100° to 150° C., and, if desired, calcined at from 200° to 600° C.

The coated carriers are then activated by treating them in a gas stream which contains free hydrogen, at from 30° to 600° C., preferably from 150° to 450° C. The gas stream preferably consists of from 50 to 100% by volume of $H_2$ and from 0 to 50% by volume of $N_2$.

If, in addition to ruthenium, one or more other metals of subgroup I, VII or VIII are also applied to the carriers, and the application is effected in succession, the carrier may, after each application or impregnation, be dried at from 100° to 150° C. and, if desired, calcined at from 200° to 600° C. The metal salt solutions may be applied or introduced by impregnation in any desired order.

If, in addition to ruthenium, one or more further metals of subgroup I, VII or VIII are applied to the carrier, copper, rhenium, cobalt, nickel or a mixture thereof is preferably used.

The ruthenium salt solution or metal salt solution is applied to the carrier or carriers in an amount such that from 0.01 to 30% by weight, based on the total weight of the catalyst, of ruthenium and, if required, other metal or other metals of subgroup I, VII or VIII are present on the carriers. This amount is preferably from 0.2 to 15, particularly preferably about 0.5, % by weight.

The total metal surface area on the catalyst is preferably from 0.01 to 10, in particular from 0.05 to 5, more particularly from 0.05 to 3 $m^2/g$ of the catalyst.

CARRIERS

The carriers which can be used for the preparation of the catalysts used according to the invention are preferably those which are macroporous and have a mean pore diameter of at least 0.1 µm, preferably at least 0.5 µm, and a surface area of not more than 15, preferably not more than 10, more preferably not more than 5, especially not more than 3, $m^2/g$. The mean pore diameter of the carrier is preferably from 0.1 to 200 µm, in particular from 0.5 to 50 µm. The surface area of the carrier is preferably from 0.2 to 15, in particular from 0.5 to 10, more particularly from 0.5 to 5, most particularly from 0.5 to 3, $m^2$ per g of the carrier.

The surface area of the carrier is determined according to the BET method by $N_2$ adsorption, in particular according to DIN 66131. The mean pore diameter and the pore size distribution were determined by Hg porosimetry, in particular according to DIN 66133. The pore size distribution of the carrier may preferably be approximately bimodal, the pore diameter distribution having maxima at about 0.6 µm and about 20 µm in the bimodal distribution, constituting a specific embodiment of the invention.

A carrier which has a surface area of about 1.75 $m^2/g$ and this bimodal distribution of the pore diameter is particularly preferred. The pore volume of this preferred carrier is preferably about 0.53 ml/g.

For example, active carbon, silicon carbide, alumina, silica, titanium dioxide, zirconium dioxide, magnesium dioxide, zinc oxide or mixtures thereof may be used as the macroporous carrier. Alumina and zirconium dioxide are preferred.

The catalysts used according to the invention preferably have high reactivity and selectivity and a long life. When the catalysts used according to the invention are employed, the hydrogenation products are preferably obtained in high yield and purity in the hydrogenation.

HYDROGENATION

The hydrogenation is carried out at suitable pressures and temperatures. Pressures above 50, preferably from 150 to 300, bar are preferred. Preferred temperatures are from 100° to 270° C., particularly preferably from 150° to 220° C.

SOLVENTS OR DILUENTS

In the novel process, the hydrogenation can be carried out in the absence of a solvent or diluent, i.e. in one embodiment it is not necessary to carry out the hydrogenation in solution. Preferably, however, a solvent or diluent is used in the novel process. The solvent or diluent used may be any suitable solvent or diluent. The choice is not critical; for example, in one embodiment the solvent or diluent may also contain small amounts of water.

Examples of suitable solvents or diluents include straight-chain or cyclic ethers, for example tetrahydrofuran or dioxane, and ammonia and mono- or dialkylamines in which the alkyl radicals are preferably of 1 to 3 carbon atoms. Mixtures of these or other solvents or diluents may also be used. The solvent or diluent may be used in suitable amounts, preferred amounts being those which lead to a 10–70% strength by weight solution of the compounds intended for the hydrogenation.

Particularly preferably, the product formed in the hydrogenation by the novel process may also be used as a solvent, if necessary in addition to other solvents or diluents. In this case, some of the product formed in the hydrogenation process is mixed with the compounds to be hydrogenated. Preferably from 1 to 30, particularly preferably from 5 to 20, times the amount, based on the weight of the compounds intended for the hydrogenation, of the hydrogenation product is admixed as solvent or diluent.

The hydrogenation is preferably carried out in the presence of ammonia or a mono- or dialkylamine, for example methyl-, ethyl-, propyl-, dimethyl-, diethyl- or dipropylamine. Suitable amounts of ammonia or mono- or dialkylamine are used, preferably from 0.5 to 50, particularly preferably from 1 to 20, parts by weight, based on 100 parts by weight of the compound or compounds intended for the hydrogenation. Anhydrous ammonia or an anhydrous amine is particularly preferably used.

The hydrogenation process can be carried out continuously or batchwise.

In the continuous process, the amount of the compound or compounds intended for the hydrogenation may be from 0.05 to 3, preferably from 0.1 to 1, l per liter of catalyst per hour.

The hydrogenation gases used may be any desired gases which contain free hydrogen and do not contain any harmful amounts of catalyst poisons, for example CO. For example, reformer waste gases may be used. Pure hydrogen is preferably used as the hydrogenation gas.

The invention is illustrated below by Examples.

EXAMPLE 1

Preparation of the catalyst

A macroporous alumina carrier which was in the form of 8×8×3 mm rings and had a surface area of 1.75 $m^2/g$, determined by the BET method, a pore volume of 0.531 ml/g and a pore diameter of 0.6 µm and 20 µm with a bimodal distribution was impregnated with an aqueous ruthenium (III) nitrate solution which had a concentration of from 0.7 to 1%, based on the weight of the solution, of metal. The volume of solution taken up by the carrier corresponded roughly to the pore volume of the carrier used. The carrier impregnated with the ruthenium(III) nitrate solution was then dried at 120° C. with agitation and was reduced at 200° C. in a stream of hydrogen. The catalyst thus prepared contained 0.5% by weight, based on the total weight of the catalyst, of ruthenium and had a ruthenium surface area of 0.76 $m^2/g$, determined by $H_2$ pulse chemisorption (Puls Chemiesorp 2700, 35° C.).

HYDROGENATION 1.2 l of the catalyst which was prepared by the above method and contained 0.5% by weight of ruthenium on a macroporous $Al_2O_3$ carrier were introduced into an electrically heated flow-through reactor which was equipped with a separator. Hydrogenation of aniline was then carried out at 230 bar and initially 160° C. without prior activation of the catalyst. The hydrogenation was carried out continuously by the liquid-phase procedure, some of the discharged hydrogenation mixture being recycled and being mixed with the starting material upstream of the reactor. 10 times the amount, based on the amount of aniline used, of hydrogenation product was added as solvent. From 500 to 600 l of hydrogen per hour were let down at the top of the separator. The amount of aniline fed continuously to the reactor corresponded to a catalyst space velocity of 0.6 l per l of catalyst per h. Depending on the reaction temperature, the following product compositions were obtained under steady-state reaction conditions:

| Temperature °C. | CHA[1] % | DCHA[2] % | Aniline % | Cyclohexane + cyclohexene % |
|---|---|---|---|---|
| 160 | 99.3 | 0.45 | 0.10 | 0.04 |
| 180 | 97.0 | 2.75 | 0.06 | 0.06 |
| 200 | 90.9 | 8.9 | — | 0.09 |

[1]CHA = Cyclohexylamine;
[2]DCHA = Dicyclohexylamine

EXAMPLE 2

Hydrogenation was carried out as described in Example 1, except that anhydrous ammonia was additionally metered in continuously. 10 parts by weight, based on 100 parts by weight of aniline, of ammonia were added. Depending on the reaction temperature, the following product compositions were obtained under steady-state reaction conditions:

| Temperature °C. | CHA[1] % | DCHA[2] % | Aniline % | Cyclohexane + cyclohexene % |
|---|---|---|---|---|
| 180 | 99.3 | 0.08 | 0.13 | 0.07 |
| 200 | 98.7 | 1.06 | — | 0.09 |

[1]CHA = Cyclohexylamine;
[2]DCHA = Dicyclohexylamine

EXAMPLE 3
Hydrogenation of toluylenediamines 2 kg of a 50% strength by weight solution of toluylenediamine (isomer mixture of 2,4- and 2,6-diaminotoluene) in tetrahydrofuran and 500 ml of the catalyst prepared according to Example 1 were initially taken in a 3.5 l pressure-resistant autoclave. The hydrogenation was then carried out batchwise at 150° C. and 200 bar for 5 hours. The conversion to the isomer mixture of the corresponding cycloaliphatic diamines was quantitative, the residual aromatics content being less than 0.01%.

EXAMPLE 4
Preparation of the catalyst

A macroporous alumina carrier which was in the form of 8×8×3 mm rings and had a surface area of 0.99 $m^2$/g, determined by the BET method, a pore volume of 0.529 ml/g and a pore diameter of 1 μm and 30 μm with a bimodal distribution was impregnated three times with an aqueous nickel(II) nitrate solution which had a concentration of 13.5%, based on the weight of the solution, of metal. The volume of solution taken up by the carrier corresponded roughly to the pore volume of the carrier used. After each impregnation the impregnated carrier was dried at 120° C. and calcined at 520° C.

The NiO/aluminum oxide catalyst thus prepared was impregnated with an aqueous ruthenium(III) nitrate solution with had a concentration of from 0.7 to 1%, based on the weight of the solution, of metal. The volume of solution taken up by the carrier corresponded roughly to the pore volume of the carrier used.

The NiO/aluminum oxide catalyst impregnated with the ruthenium(III) nitrate solution was then dried at 120° C. with agitation and was reduced at 200° C. in a stream of hydrogen. The catalyst thus prepared contained 0.5% by weight of ruthenium and 11% by weight of nickel, based on the total weight of the catalyst.

EXAMPLE 5

Hydrogenation was carried out as described in Example 1, except that aniline was reacted continuously in a flow-through reactor containing the 0.5% Ru/11% Ni/$Al_2O_3$ catalyst. At a temperature of 190° C. and a catalyst load of 0.2 kg/l×h a total conversion was obtained and a selectivity for cyclohexylamine of 94%.

EXAMPLE 6

Hydrogenation was carried out as described in Example 3, except that di-(4-aminophenyl)methane was converted quantitatively in an autoclave to a cis/trans-mixture of di-(4-aminocyclohexyl)methane.

We claim:

1. A process for catalytically hydrogenating aromatic amines in which at least one amino group is bonded to an aromatic nucleus which comprises bringing at least one of said aromatic amines as the reactant in a liquid phase into contact with free hydrogen in the presence of a carrier supported metal catalyst consisting essentially of ruthenium and optionally at least one additional metal of subgroup I, VII or VIII of the Periodic Table or mixtures thereof, said metal catalyst being applied to a carrier having a mean pore diameter of at least 0.1 μm and a surface area of not more than 15 $m^2$/g in an amount of from 0.01 to 30% by weight, based on the total weight of both the carrier and the applied metal.

2. A process as claimed in claim 1, wherein ruthenium any additional metal of subgroup I, VII or VIII are applied to the catalyst in an amount of from 0.2 to 15% by weight, based on the total weight of the catalyst.

3. A process as claimed in claim 1, wherein the mean pore diameter of the carrier is at least 0.5 μm.

4. A process as claimed in claim 1, wherein the pore size distribution of the carrier is approximately bimodal.

5. A process as claimed in claim 1, wherein the surface area of the carrier is not more than 10 $m^2$/g.

6. A process as claimed in claim 1, wherein the carrier is selected from the group consisting of active carbon, silicon carbide, alumina, silica, titanium dioxide, zirconium dioxide, magnesium dioxide, zinc oxide and mixtures thereof.

7. A process as claimed in claim 1, wherein the one or more metals of subgroup I, VII or VIII are selected from the group consisting of copper, rhenium, cobalt and nickel or mixtures thereof.

8. A process as claimed in claim 1, wherein the total metal applied to the carrier has a surface area of from 0.01 to 10, preferably from 0.05 to 5, $m^2$ per g of catalyst.

9. A process as claimed in claim 1, wherein the carrier supported metal catalyst consists of a macroporous alumina carrier having a surface area of about 1.75 $m^2/g$, a pore volume of about 0.531 ml/g, a bimodal pore size distribution with pore diameters of about 0.6 μm and about 20 μm, onto which carrier ruthenium is applied in an amount of about 0.5% by weight, based on the total weight of the catalyst, and the ruthenium surface area on the carrier is about 0.76 $m^2$ per g of catalyst.

10. A process as claimed in claim 1, wherein the aromatic compound in which at least one amino group is bonded to an aromatic nucleus is an aromatic mono amine or diamine.

11. A process as claimed in claim 1, wherein the aromatic mono amine or diamine is selected from the group consisting of aniline, naphthylamine, diaminotoluenes, bis-p-aminophenylmethane and mixtures thereof.

12. A process as claimed in claim 1, wherein the hydrogenation is carried out in the presence of a solvent or diluent.

13. A process as claimed in claim 12, wherein the solvent or diluent is selected from the group consisting of linear and cyclic ethers, ammonia and mono- and dialkylamines in which the radical is an alkyl group, and mixtures thereof.

14. A process as claimed in claim 12, wherein the solvent or diluent used is the hydrogenation product, which is present in an amount of from 1 to 30 times, based on the weight of the compound to be hydrogenated.

15. A process as claimed in claim 1, which is carried out at not less than 50, bar and at from 100° to 270° C.

16. A process as claimed in claim 1, which is carried out continuously.

17. A process as claimed in claim 9, wherein the aromatic amine or diamine is selected from the group consisting of aniline, naphthylamine, diaminotoluenes, bis-p-aminophenylmethane and mixtures thereof.

18. A process as claimed in claim 1, wherein the carrier is selected from the group consisting of alumina and zirconium dioxide.

19. A process as claimed in claim 1, which is carried out at a pressure of from 150 to 300 bar and at a temperature of from 150° to 220° C.

20. A process as claimed in claim 1, which is carried out batchwise.

21. A process as claimed in claim 12, wherein the diluent or solvent is an ether selected from the group consisting of tetrahydrofuran and dioxane and mixtures thereof.

22. A carrier supported metal hydrogenation catalyst consisting essentially of the metal ruthenium and optionally at least one additional metal of subgroup I, VII or VIII of the Periodic Table or mixtures thereof, said metal catalyst being applied to a carrier having a mean pore diameter of at least 0.1 up to 200 μm and a surface area of from 0.2 up to 15 $m^2/g$ in an amount of from 0.01 to 30% by weight, based on the total weight of both the carrier and the applied metal.

23. A catalyst as claimed in claim 22, wherein the metal catalyst consists essentially of ruthenium, optionally with a second metal selected from the group consisting of copper, rhenium, cobalt, nickel and mixtures thereof, as applied to a carrier selected from the group consisting of alumina and zirconium dioxide.

24. A catalyst as claimed in claim 23, wherein the carrier supported metal catalyst consists essentially of alumina and ruthenium.

* * * * *